US006376439B2

(12) United States Patent
de Ferran et al.

(10) Patent No.: US 6,376,439 B2
(45) **Date of Patent: *Apr. 23, 2002**

(54) SOAP BAR COMPOSITION

(75) Inventors: Marcia de Ferran; Adolfo Gutmann; Sergio Roberto Leopoldino, all of Sao Paulo (BR)

(73) Assignee: Unilever Home & Personal Care USA division of Conopco, Inc., Greenwich, CT (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/362,174

(22) Filed: Jul. 27, 1999

Related U.S. Application Data

(63) Continuation-in-part of application No. 08/882,408, filed on Jun. 25, 1997, now Pat. No. 5,952,276.

(30) Foreign Application Priority Data

Jun. 26, 1996 (BR) .......................................... 96/02897

(51) Int. Cl.[7] .......................... C11D 17/00; A61K 7/50

(52) U.S. Cl. ...................... 510/141; 510/133; 510/152; 510/153; 510/447; 510/466; 510/481; 510/440; 510/437

(58) Field of Search ............................... 510/141, 133, 510/152, 153, 447, 466, 481, 440, 437

(56) References Cited

U.S. PATENT DOCUMENTS

| | | | | |
|---|---|---|---|---|
| 4,919,838 | A | 4/1990 | Tibbetts et al. | 353/117 |
| 5,154,849 | A | 10/1992 | Visscher et al. | 252/174.14 |
| 5,227,086 | A | 7/1993 | Kacher et al. | 252/112 |
| 5,264,144 | A | 11/1993 | Moroney et al. | 252/117 |
| 5,264,145 | A | 11/1993 | French et al. | 252/117 |
| 5,340,492 | A | 8/1994 | Kacher et al. | 252/112 |
| 5,425,892 | A | 6/1995 | Taneri et al. | 252/134 |
| 5,441,671 | A | 8/1995 | Cheney et al. | 252/549 |
| 5,496,488 | A | 3/1996 | Kacher et al. | 252/125 |
| 5,501,812 | A | 3/1996 | Vermeer et al. | 252/174.17 |
| 5,703,026 | A | 12/1997 | Setser et al. | 510/152 |
| 5,786,312 | A | 7/1998 | Post et al. | 510/157 |

FOREIGN PATENT DOCUMENTS

| | | |
|---|---|---|
| EP | 0283165 | 9/1988 |
| EP | 0578481 | 1/1994 |
| GB | 2058822 | 4/1981 |
| GB | 2143250 | 5/1984 |
| JP | 1060696 | 3/1989 |
| JP | 1294797 | 11/1989 |
| JP | 4370199 | 12/1992 |
| WO | 92/08444 | 5/1992 |
| WO | 94/17172 | 8/1994 |
| WO | 95/26710 | 10/1995 |

*Primary Examiner*—Yogendra N. Gupta
*Assistant Examiner*—Derrick G Hamlin
(74) *Attorney, Agent, or Firm*—Ronald A. Koatz

(57) ABSTRACT

A composition for a soap bar comprises:

(i) from about 0.01 to about 7% by weight of silicone;

(ii) from about 0.5% to about 5%,by weight of a first emollient selected from the group consisting of from polyols, selected from the group consisting of glycerin, sorbitol, and mixtures thereof;

(iii) about 0.1 to about 5% by weight, of a second emollient selected from the group consisting of vegetable, animal or mineral oils, free fatty acids and mixtures thereof;

(iv) about 60% to 90% by weight fatty acid soap; wherein bar has L% light transmittance under 40%.

9 Claims, No Drawings

SOAP BAR COMPOSITION

The present application is a continuation-in-part of U.S. Ser. No. 08/882,408, filed Jun. 25, 1997, now issued as U.S. Pat. No. 5,952,276.

The present invention refers to a novel soap composition, particularly to an opaque toilet soap bar for cleansing body skin, which has an improved mildness.

A general problem in the formulation of soap bars has been that of finding a balance between providing structure whilst both maintaining lathering properties and imparting beneficial mildness to the skin, at a practical overall cost.

The conventional soap making process is well documented in the literature. Patent application WO 92/08444 discloses a skin cleansing bar, which may be soap based and contains 0.5–20% of a silicone gum/silicone fluid. Polyalkyl siloxanes are preferred. This composition improves skin conditioning and moisturization, and reduces both irritation and dryness. Optional ingredients include fatty acid as plasticizer, glycerine as moisturizer and a whole range of vegetable oils as occlusive moisturizers.

Patent application EP 578,481 discloses a solid soap containing 0.5–7% of a water insoluble silicone

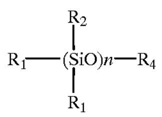

and optional ingredients such as glycerine. This product is intended to reduce cracking and flaking of the skin and to improve moisture retention.

Patent application GB 2,058,822 discloses a soap composition containing 0.01–6% of polydiorganosiloxane of molecular weight 2000 or higher and containing nitrogen and improves the feel of the skin after use.

Patent application GB 2,143,250 discloses a combination of vegetable oil and silicone oil which is used in a personal cleansing composition.

Patent application WO 94/17172 (Unilever) discloses a syndet-based bar composition containing 0.1–9% of silicone and from 0–25% of soap and 0–35% of free fatty acids.

Patent application JP 01/294,797 discloses mixtures of silicone oils and optionally polyols (e.g., glycerol) which are used in soaps based on counterions derived from weak bases.

Patent application JP 01/060,696 discloses mixtures of silicone oils and optionally polyols (e.g., glycerol) which are used in transparent soaps.

U.S. Patent No. 5,154,849 to Visscher teaches "mild" skin cleansing bars comprising 0.5 to 20% silicone component which consists of silicone gum and silicone fluid in ratio of gum:fluid 10:1 to 1:10 wherein the silicone component has particle size at least about 20 microns. Fatty acid soap, when used, is preferred at levels of 5–40%, 5–20% most preferred. These bars clearly, however, are mainly synthetic bars. This is in contrast to the primarily fatty acid soap bars of the invention which would not normally be considered "mild" bars by the art. The subject invention concerns formulation of these normally not so mild bars with ingredients designed to impart lubricated, hydrated feel while maintaining creamy, dense foam.

Finally, JP 04/370,199 teaches transparent soap bars (i.e., having visible light transmission, L%, greater than 40% in all examples as measured using defined test) having fatty acid soap, a betaine group containing siloxane compound and glycerin. Bars of the invention preferably do not contain betainecontaining siloxanes (preferably, they contain standard silicones). Moreover, bars of the invention are opaque bars, having light transmittance of less than 40%, preferably less than 30%, more preferably less than 20%, more preferably less than 15% and most preferably less than 10%.

DESCRIPTION OF THE INVENTION

Due to the characteristics of surfactants present in conventional toilet soaps, although such soaps are extremely efficient cleansers of skin, this high efficiency may leave the skin unprotected immediately after the wash, thus provoking a stretched/dried out sensation.

In order to overcome this drawback, this present invention provides a new soap composition comprising fatty acid soap associated with mildness actives.

Laboratory tests have shown, surprisingly, that when silicones and other emollient agents are mixed together, toilet soaps begin to provide other benefits to the skin, over and above their cleansing qualities. These include the agreeable sensation of a lubricated, hydrated and a silky skin.

The results have been verified in internal evaluations done by sensory panelists.

Among the qualities of silicones which are applicable to the skin, the following may be highlighted: it is a hydrophobic substance, and thus water resistant, which remains after the rinsing process; it is a lubricant for the skin and hair. At the same time, it provides an improved tactile sensation and does not block the pores of skin.

These relevant features are optimized when the silicone is combined with other emollient agents. The principal mechanism for obtaining this state is by adsorption of these emollient agents into the silicone molecule.

Additionally, it was found that the soap composed in accordance with this invention gives a more creamy denser foam, when compared with current state of the art toilet soaps.

Thus, the present invention refers to a composition for soap, based on a conventional soap, with 60% to 90%, preferably 65% to 85% by weight of total fatty acids, to which are added from 0.1% to 15% by weight, of a combination of silicones and other emollients. To dry skin, this will give the sensation of soft, silky skin, to a greater extent than other soaps.

More specifically the silicone should compare 0.01 to 7%, preferably 0.1 to 5%, more preferably 0.5 to 5% by wt. of composition; a first emollient (glycerin, sorbitol and mixtures thereof) comprises about 0.1 to 5%, preferably 0.5 to 5% by wt. of composition and second emollient comprises 0.1 to about 3% by wt. of composition.

Different types of silicones, such as linear, cyclic, substituted silicones and their combinations may be used in the present composition. Preferably, the silicone is a non-betaine containing silicone.

The emollients (e.g., second emollients) which are suitable for toilet soap, under this invention, may be selected from polyols, fatty acids, vegetable, mineral and animal oils, and other emollients which are similar or which may be adsorbed into the silicone chain.

Among the free fatty acids, babassu fatty acid and lauric acid are preferred.

From the vegetable oils, the sunflower oil, corn oil and almond oil among others may be used.

Glycerin and sorbitol (e.g., first emollient) are preferred among the polyols.

Bars of the invention also comprise about 5% to about 20%, preferably about 5% to 15% water.

The composition of the toilet soap bar, prepared in accordance with this invention, may also include a certain percentage of an appropriate dye or colorant agent, added to the soap mix to impart the desired color to the soap bar.

The quantities of perfume and coloring agent to be added to the soap mix, prepared in accordance with this invention, are not critical, and should be such that they produce the desired coloring and aromatizing effect.

The bars of the invention are opaque bars. More specifically, as compared to bars of JP 04/370,199 which have visible light transmission L% of greater than 40% in all examples, bars of the invention have L% of less than 40%, preferably less than 30%, preferably less than about 20%, more preferably less than about 15% and most preferably about 10% and below.

The L% value is that measured as described in JP 04/370, 199. More specifically, a bar composition is cut into 2 cm thick test pieces, the surface is smoothly polished and visible light transmittance L% of test pieces may be evaluated by a color difference meter (e.g., made by Nippon Denshiki Company), color measurement, color difference meter ND-2001 DP type.

Below, a novel soap composition according to the present invention is described by way of an example of how it should be prepared.

This example is merely illustrative and in no way limits the scope of this invention.

Unless stated otherwise, all percentages in specification and example are intended to be by weight.

EXAMPLE

In this example, a cold-rolled soap method is used to prepare a soap bar.

A previously prepared soap mix for making a toilet soap cake according to the present invention, composed of 65% to 85%, by weight, of salts of fatty acids, reckoned as total fatty acids, is placed in a crunching machine (Sigma, for example). The glycerine and/or polyols (first emollient), silicone and other emollients (second emollient) are added in a proportion, by weight, of from 1% to 15%. The moisture contents of the mix is then set at between 8% to 20%, by weight.

Finally, the desired amount of an appropriate coloring agent (for example: Red Iragon PS paste and/or Orange Iragon II DC) is added, together with a desired amount of a soap compatible perfume, such as Gemini 699.

During the whole process of adding these ingredients, the composition is thoroughly mixed with a suitable stirrer. Once the mix is homogenous, the conventional stages of the process for obtaining soap or toilet soap in cakes are carried out, these being: rolling (with a Buehler/Mazzoni Roller), compacting and extruding (using a Bonot extruder), cutting of the extruded bar and stamping and wrapping the bar (using a Sigma or Acmad Machine).

In this way, a cake of soap with a composition in accordance with this invention and having the characteristics defined hereinabove are obtained.

What is claimed is:

1. An opaque soap bar composition comprising:

(i) from about 0.01 to about 7%, by weight, of silicone;

(ii) from about 0.5% to about 5%, by weight, of a first emollient selected from the group consisting of glycerin, sorbitol, and mixtures thereof;

(iii) about 0.1 to about 5%, by weight, of a second emollient selected from the group consisting of vegetable, animal or mineral oils, free fatty acids and mixtures thereof;

(iv) about 60 to 90% by weight fatty acid soap; wherein said bar has L% light transmittance under 40%.

2. A soap bar composition as claimed in claim 1, wherein said silicone is selected from linear, cyclic, substituted silicones and mixtures thereof.

3. A soap bar composition according to claim 1, wherein said free fatty acids are selected from babassu fatty acid or lauric acid.

4. A soap bar composition according to claim 1, wherein said vegetable oil is selected from the group consisting of sunflower oil, corn oil, almond oil and mixtures thereof.

5. A bar according to claim 1, comprising about 0.1 to about 5% silicone.

6. A bar according to claim 1 further comprising about 5% to 20% by wt. water.

7. A bar according to claim 1, further comprising an effective amount of a dye and/or coloring agent.

8. A composition according to claim 1 further comprising perfume.

9. A composition according to claim 1, where L% is 30% and below.

* * * * *